United States Patent
Lee et al.

(10) Patent No.: US 11,666,620 B2
(45) Date of Patent: Jun. 6, 2023

(54) METHOD FOR TREATMENT OF FINE DUST-CAUSED SKIN CELL DAMAGE, REINFORCEMENT OF SKIN BARRIER, ANTI-AGING, AND ANTI-INFLAMMATION

(71) Applicant: AMOREPACIFIC CORPORATION, Seoul (KR)

(72) Inventors: Yeongran Lee, Yongin-si (KR); Hyoung-June Kim, Yongin-si (KR); Jun Seong Park, Yongin-si (KR); Kyeonghwan Hwang, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 62 days.

(21) Appl. No.: 16/766,158

(22) PCT Filed: Nov. 22, 2018

(86) PCT No.: PCT/KR2018/014447
§ 371 (c)(1),
(2) Date: Sep. 10, 2020

(87) PCT Pub. No.: WO2019/103486
PCT Pub. Date: May 31, 2019

(65) Prior Publication Data
US 2021/0038673 A1    Feb. 11, 2021

(30) Foreign Application Priority Data

Nov. 22, 2017  (KR) .................. 10-2017-0156619
Nov. 22, 2017  (KR) .................. 10-2017-0156631
Nov. 22, 2017  (KR) .................. 10-2017-0156642

(51) Int. Cl.
| | | |
|---|---|---|
| A61K 36/82 | (2006.01) |
| A23L 33/105 | (2016.01) |
| A61K 8/9789 | (2017.01) |
| A61K 8/60 | (2006.01) |
| A61K 31/704 | (2006.01) |
| A61Q 19/08 | (2006.01) |

(52) U.S. Cl.
CPC ............ *A61K 36/82* (2013.01); *A23L 33/105* (2016.08); *A61K 8/602* (2013.01); *A61K 8/9789* (2017.08); *A61K 31/704* (2013.01); *A61Q 19/08* (2013.01); *A23V 2002/00* (2013.01)

(58) Field of Classification Search
None
See application file for complete search history.

(56) References Cited

FOREIGN PATENT DOCUMENTS

| | | |
|---|---|---|
| JP | 2006-45168 A | 2/2006 |
| KR | 10-2013-0022471 A | 3/2013 |
| KR | 10-2013-0035325 A | 4/2013 |
| KR | 10-2016-0119703 A | 10/2016 |
| KR | 10-2017-0040002 A | 9/2017 |

OTHER PUBLICATIONS

Boo (2019) Antioxidants 8: 379: (18 pages). (Year: 2019).*
Chattopadhyay et al. (2004) Life Sciences 74: 1839-1849. (Year: 2004).*
Diao et al. (2021) Biomedicine & Phamacotherapy 138: 111534 (9 pages) (Year: 2021).*
Magnani et al. (2016) Toxicological Sciences 149(1): 227-236. (Year: 2016).*
Romani et al. (2018) Mechanisms of Ageing and Development 172: 86-95. (Year: 2018).*
Sur et al. (2001) Phytother. Res. 15: 174-176. (Year: 2001).*
Office Action for Korean Patent Application No. 10-2017-0156631 (dated Oct. 30, 2021).
Office Action for Korean Patent Application No. 10-2017-0156619 (dated Oct. 30, 2021).
Ramakrishnan et al., "UHPLC-MS/SRM method for analysis of phenolics from Camellia sinensis leaves from Nilgiri hills", The Royal Society of Chemistry, 2016, vol. 8, pp. 8033-8041.
D'Erme et al., "IL-36c (IL-1F9) is a Biomarker for Psoriasis Skin Lesions", The Society for Investigative Dermatology, 2015, vol. 135, pp. 1025-1032.
Eckert et al., "S100 Proteins in the Epidermis", The Society for Investigative Dermatology, 2004, vol. 123, pp. 23-33.
Hyoung-June Kim et al., "Transcriptome analysis of airborne PM2. 5-induced detrimental effects on human keratinocytes", Toxicology Letters, 2017, vol. 273, pp. 26-35.
International Search Report from International Application No. dated May 17, 2019.
Written Opinion from International Application No. dated May 17, 2019.

* cited by examiner

*Primary Examiner* — Russell G Fiebig
(74) *Attorney, Agent, or Firm* — Merchant & Gould, P.C.

(57) ABSTRACT

The present specification discloses a composition for external application to skin, containing a tea plant root extract as an active ingredient, for treatment of skin damage caused by fine dust, whereby the expression level of one or more selected from a group consisting of IL-36G (NM_019618), S100A7 (NM_002963), S100A8 (NM_002964) and XDH (NM_000379), which are genes in skin cells the expression level of which is affected by fine dust, is regulated to a normal level.

13 Claims, 5 Drawing Sheets

METHOD FOR TREATMENT OF FINE DUST-CAUSED SKIN CELL DAMAGE, REINFORCEMENT OF SKIN BARRIER, ANTI-AGING, AND ANTI-INFLAMMATION

CROSS-REFERENCE TO RELATED APPLICATION

This application claims priority to Korean Patent Applications No. 10-2017-0156619, filed on Nov. 22, 2017, No. 10-2017-0156631, filed on Nov. 22, 2017, and No. 10-2017-0156642, filed on Nov. 22, 2017, and all the benefits accruing therefrom under 35 U.S.C. § 119, the contents of which in their entireties are herein incorporated by reference.

TECHNICAL FIELD

The present specification discloses a composition for treating skin cell damage caused by fine dust. More particularly, disclosed is a composition containing a tea plant root extract, which treats skin cell damage by significantly changing the expression level of biomarkers, etc. which are skin cell genes the expression level of which is changed by fine dust as compared to skin cells in normal state.

BACKGROUND ART

Skin is a part of the body that is directly exposed to the external environment. It not only serves as a protective layer for protecting important organs of our body, but also regulates water evaporation and protects the body from external infections. However, even though the skin prevents viral invasion from the outside, excessive exposure of the skin to ultraviolet rays or pollutants causes skin irritation. Particularly, the skin is damaged by Asian dust which is accompanied by strong wind and dirt.

Asian dust is a phenomenon in which small-sized sands or red clays float from the inland deserts of China, Mongolia, etc., are carried far away by the upper winds and then drop near the ground. In Korea, Asian dust occurs periodically every spring. Asian dust is a combination of organic and inorganic materials, and its physical characteristics and constituents are very diverse depending on the time and place of occurrence. It also includes metals that can have biological effects. The larger-sized particles of Asian dust usually stay in or around their origin, and the smaller-sized particles thereof flow even into Korea. It is reported that, when inhaled, this dust is deposited in the lower bronchial tubes and even in the gas exchange part of the lungs, which may cause damage to the respiratory system. In addition, it was found that skin cell damage was increased in the skin of people living in areas with lots of Asian dust or dirt.

Among the layers of the skin, the epidermis plays an important role in preventing evaporation of water out of the human body. The epidermis is divided into the stratum corneum, the stratum granulosum, the stratum spinosum and the stratum basale from the outside. The cells of the stratum corneum act like bricks, and the intercellular lipids between keratinocytes act like mortar to constitute the skin barrier. In addition, the keratinocytes of healthy people have natural moisturizing factors (NMFs) at high concentrations, which help to retain moisture in the skin. For example, water-soluble substances such as amino acids effectively combine with water and prevent the skin from drying.

Nowadays, because of various reasons such as artificial temperature control for cooling/heating due to changes of the environment or life patterns, skin stresses caused by various stresses from social lives and environmental pollution, frequent washing due to makeups, and natural skin aging, etc. due to increase in age, the water content of the stratum corneum decreases, so that the skin becomes dry, the skin surface becomes rough, and the skin becomes loose and looks rusty due to lack of moisture, etc. Thus, there is an increasing need for skin moisturizers. Further, excessive physical and chemical stimuli from the outside, ultraviolet rays, stress and nutritional deficiencies deteriorate the normal functions of the skin and accelerate such phenomena as loss of elasticity, keratinization, wrinkle formation, etc. In particular, the dermis-epidermis border is severely damaged by ultraviolet rays.

XDH is known as an indicator of exogenous skin aging, indicative of oxidative stress induced by prolonged exposure to irritation sources (see non-patent document 1).

IL-36G is known as a useful biomarker for psoriasis, etc. caused by weakened skin barrier (see non-patent document 2). In addition, S100A7 and S100A8 are known as indicators related with atopic dermatitis and psoriasis caused by the disorder of skin barrier function. In particular, since it is disclosed that the increased expression level of S100A8 is associated with activation of keratinocytes and is not caused by inflammation (see non-patent document 3), it is distinguished from inflammation of the skin.

REFERENCES OF RELATED ART

Non-Patent Documents (Non-patent document 1) Kim, H. J., et al, "Transcriptome analysis of airborne $PM_{2.5}$-induced detrimental effects on human keratinocytes", *Toxicology Letters* 273, 26-35, 2017.
(Non-patent document 2) AM D'Erme et al, "IL-36c (IL-1F9) Is a Biomarker for Psoriasis Skin Lesions", *Journal of Investigative Dermatology*, Volume 135, 2015.
(Non-patent document 3) Eckert et al, "S100 Proteins in the Epidermis", *J Invest Dermatol,* 123(1): 23-33, 2004 July.

DISCLOSURE

Technical Problem

The inventors of the present disclosure have found that fine dust has harmful effects on skin, which affect the expression of skin cell genes, thereby causing such symptoms as skin cell damage, etc., and that a composition according to the present disclosure has an effect of alleviating skin cell damage caused by fine dust.

In addition, they have found that an irritation source weakening the skin barrier has harmful effects on skin, which affect the expression of skin cell genes, thereby causing such symptoms as weakening of the skin barrier, etc., and that a composition according to the present disclosure has an effect of reinforcing the skin barrier.

In addition, they have found that an irritation source causing inflammation or aging has harmful effects on skin, which affect the expression of skin cell genes, thereby causing such symptoms as inflammation, aging, etc., and that a composition according to the present disclosure has anti-aging and anti-inflammatory effects.

Accordingly, in an aspect, the present disclosure is directed to providing a composition for treating skin cell damage caused by fine dust, a composition for reinforcing skin barrier, an anti-aging composition, and an anti-inflammatory composition.

Technical Solution

In an aspect, the present disclosure provides, as a composition containing a tea plant root extract as an active ingredient, a composition for treating skin damage caused by fine dust, which regulates the expression level of one or more selected from a group consisting of IL-36G (NM_019618), S100A7 (NM_002963), S100A8 (NM_002964) and XDH (NM_000379), which are genes in skin cells the expression level of which is affected by fine dust, to a normal level.

In another aspect, the present disclosure provides, as a composition containing a tea plant root extract as an active ingredient, a composition for reinforcing skin barrier, which regulates the expression level of one or more selected from a group consisting of IL-36G (NM_019618), S100A7 (NM_002963) and S100A8 (NM_002964), which are genes in skin cells the expression level of which is affected by an irritation source weakening skin barrier, to a normal level.

In another aspect, the present disclosure provides, as compositions containing a tea plant root extract as an active ingredient, an anti-aging composition and an anti-inflammatory composition, which regulate the expression level of XDH (NM_000379), which is a gene in skin cells the expression level of which is affected by an irritation source causing inflammation or aging, to a normal level.

Advantageous Effects

In an aspect, by using a composition for treating skin damage caused by fine dust provided by the present disclosure, skin cell damage can be treated by returning the expression level of the genes changed by fine dust to a normal level.

In an aspect, by using a composition for reinforcing skin barrier provided by the present disclosure, skin cell damage can be treated by returning the expression level of the genes changed by an irritation source weakening skin barrier to a normal level.

In an aspect, by using an anti-aging composition and an anti-inflammatory composition provided by the present disclosure, skin cell damage can be treated by returning the expression level of the genes changed by inflammation or aging to a normal level.

Figure 1:
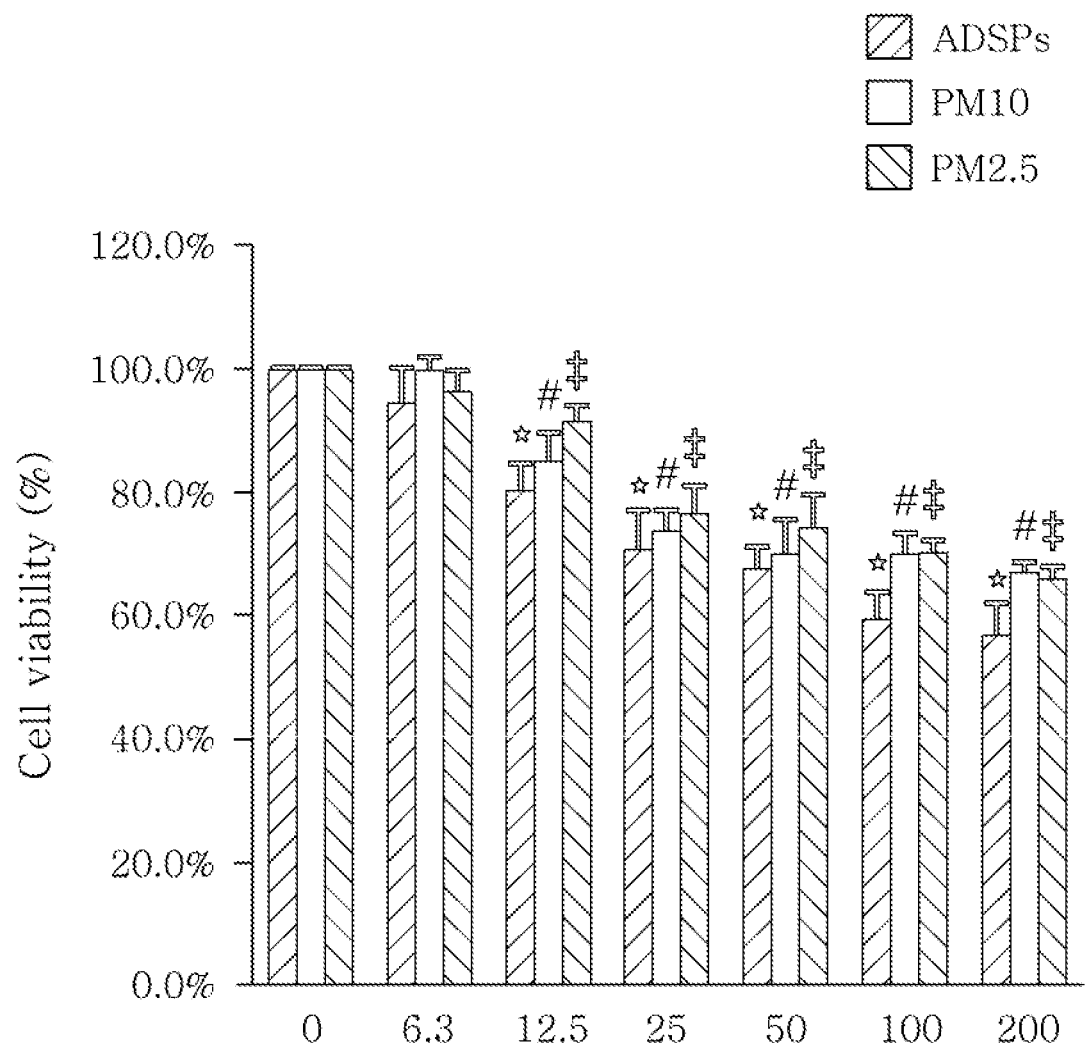
FIG. 1 shows the effect of a fine dust extract on cell viability. ADSP (Asian dust storm particle) stands for Asian dust, PM10 stands for fine dust having a particle size of 10 μm, and PM2.5 stands for fine dust having a particle size of 2.5 μm.
Figure 2A:
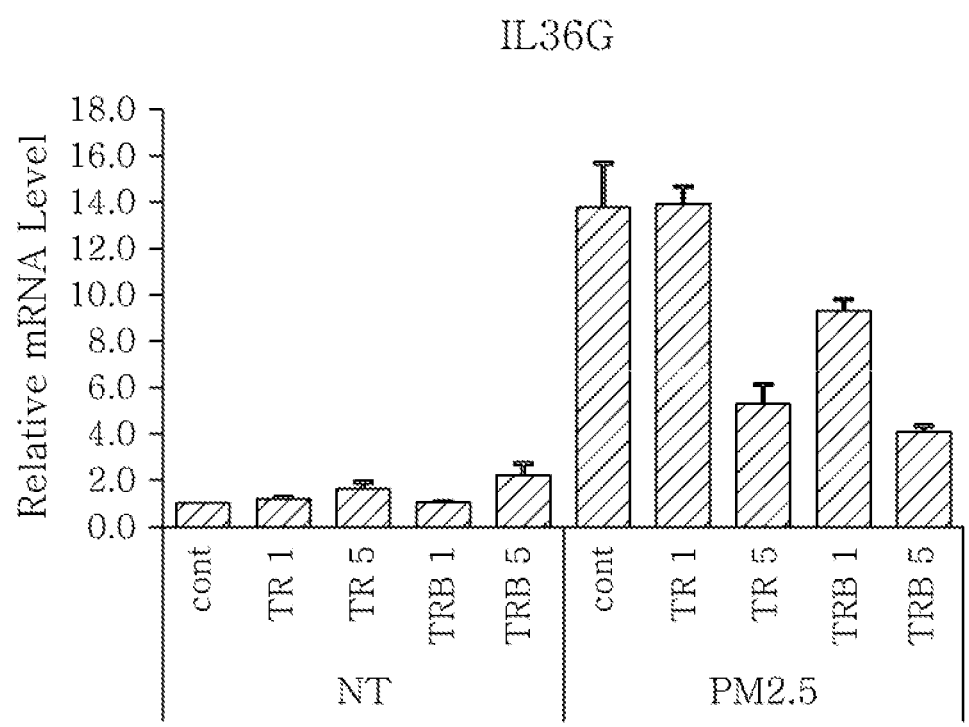
FIG. 2A shows that the mRNA expression level of the IL-36G gene in skin cells, which has been changed due to irritation by PM2.5 fine dust, is returned to a normal level by treatment with a tea plant root extract.
Figure 2B:
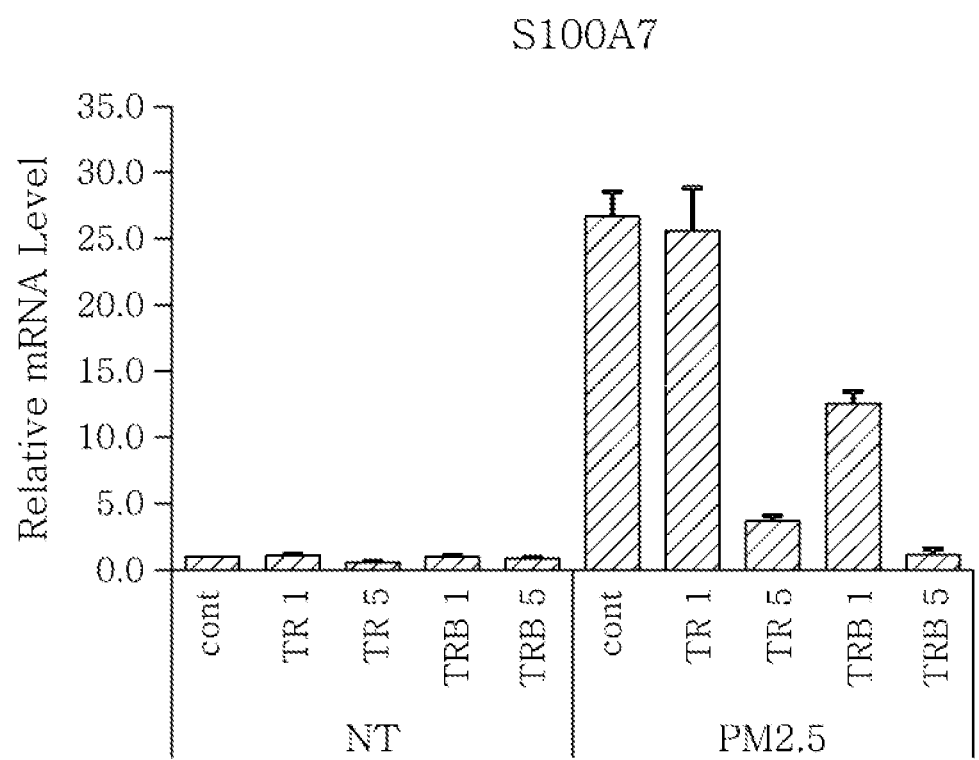
FIG. 2B shows that the mRNA expression level of the S100A7 gene in skin cells, which has been changed due to irritation by PM2.5 fine dust, is returned to a normal level by treatment with a tea plant root extract.
Figure 2C:
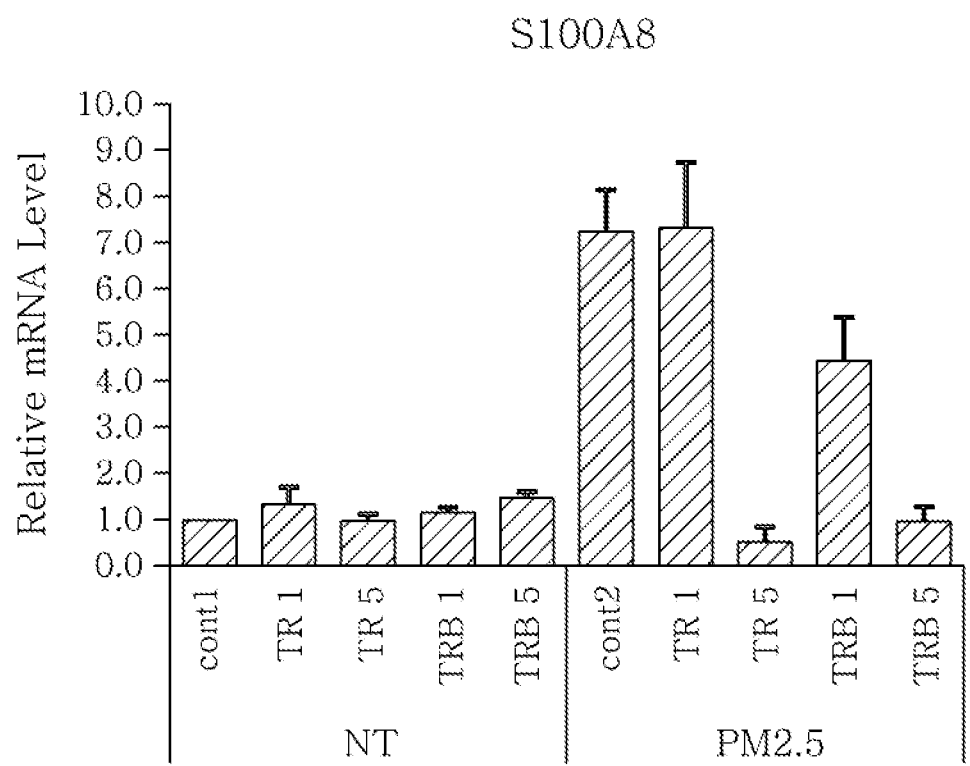
FIG. 2C shows that the mRNA expression level of the S100A8 gene in skin cells, which has been changed due to irritation by PM2.5 fine dust, is returned to a normal level by treatment with a tea plant root extract.
Figure 2D:
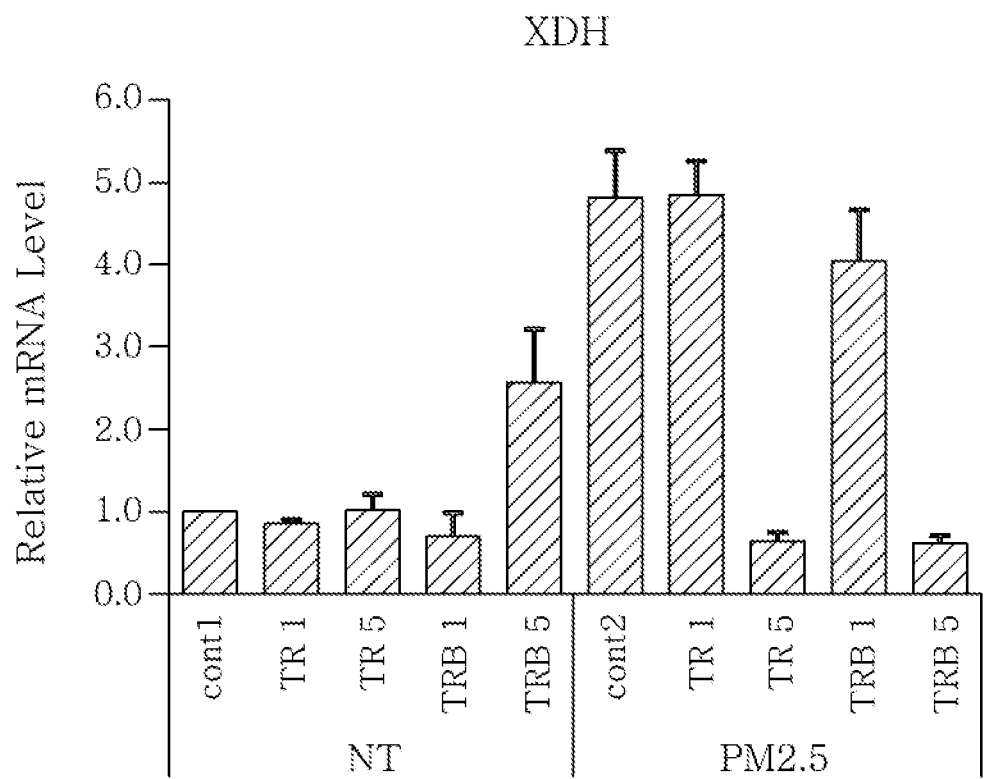
FIG. 2D shows that the mRNA expression level of the XDH gene in skin cells, which has been changed due to irritation by PM2.5 fine dust, is returned to a normal level by treatment with a tea plant root extract.

In the figures, "TR1" stands for a tea plant root ethanol extract (Example 1) at 1 ppm, "TR5" stands for a tea plant root ethanol extract (Example 1) at 5 ppm, "TRB1" stands for a butanol fraction of a tea plant root ethanol extract (Example 2) at 1 ppm, "TRB5" stands for a butanol fraction of a tea plant root ethanol extract (Example 2) at 5 ppm, "NT" stands for not treated with fine dust, and "cont1" and "cont2" stand for control groups.

BEST MODE

Hereinafter, the present disclosure is described in detail.

In an aspect of the present disclosure, a composition may contain a tea plant root extract as an active ingredient.

Tea plant (*Camellia sinensis*) is a perennial evergreen plant belonging to the family Theaceae. Tea plant is distributed is in tropical, subtropical and temperate regions and its main ingredients include catechins, saponins, caffeine, amino acids, vitamins, minerals, etc. These chemical substances are known to exhibit various physiological activities and pharmacological effects. At present, they are being studied actively as physiologically active substances contributing to health.

In an aspect, the tea plant root extract may be an extract containing a saponin.

In an aspect, the tea plant root extract may contain the saponin in an amount of 30-70 wt % based on the total weight of the extract. Specifically, the tea plant root extract may contain the saponin in an amount of 50-60 wt % based on the total weight of the extract. When the content of the saponin is within the above range, superior effect of treating skin damage caused by fine dust, effect of reinforcing skin barrier and anti-aging and anti-inflammatory effects can be achieved with the tea plant root extract.

Specifically, the content may be 30 wt % or higher, 31 wt % or higher, 32 wt % or higher, 33 wt % or higher, 34 wt % or higher, 35 wt % or higher, 36 wt % or higher, 37 wt % or higher, 38 wt % or higher, 39 wt % or higher, 40 wt % or higher, 41 wt % or higher, 42 wt % or higher, 43 wt % or higher, 44 wt % or higher, 45 wt % or higher, 46 wt % or higher, 47 wt % or higher, 48 wt % or higher, 49 wt % or higher, 50 wt % or higher, 51 wt % or higher, 52 wt % or higher, 53 wt % or higher, 54 wt % or higher, or 55 wt % or higher, and may be 70 wt % or lower, 69 wt % or lower, 68 wt % or lower, 67 wt % or lower, 66 wt % or lower, 65 wt % or lower, 64 wt % or lower, 63 wt % or lower, 62 wt % or lower, 61 wt % or lower, 60 wt % or lower, 59 wt % or lower, 58 wt % or lower, 57 wt % or lower, 56 wt % or lower, or 55 wt % or lower, although not being limited thereto.

In an aspect of the present disclosure, the tea plant root may be extracted with a specific extraction solvent to obtain the tea plant root extract.

In an aspect of the present disclosure, the tea plant root extract may be prepared by extracting tea plant root with water or an organic solvent as a primary extraction solvent. Specifically, the primary extraction solvent may be one or more extraction solvent selected from a group consisting of water, a $C_1$-$C_6$ anhydrous or hydrated lower alcohol, acetone, butylene glycol, ethyl acetate, diethyl acetate, diethyl ether, benzene, chloroform and hexane. More specifically, the extraction may be performed by using one or more solvent of a polar solvent including water, $C_1$-$C_6$ anhydrous or hydrated lower alcohol, acetone and butylene glycol and a less polar solvent including ethyl acetate, diethyl acetate, diethyl ether, benzene, chloroform and hexane. More specifically, the solvent may be a 50-90% aqueous ethanol solution or a 60-80% or 65-75% aqueous ethanol solution. When the solvent is a 50-90% aqueous ethanol solution, active ingredients may be effectively extracted from the tea plant root. In an exemplary embodiment, the solvent may be about 70% aqueous ethanol solution.

In an aspect, the tea plant root extract may be prepared by extracting with the primary extraction solvent and then fractionating with a secondary extraction solvent. Specifically, the secondary extraction solvent may be anhydrous or hydrated butanol. Through the fractionation, the content of a specific ingredient contained in the extract may be increased further. Specifically, the content of a saponin contained in the tea plant root extract may be increased further. For example, the content of a saponin in the extract fractionated with the secondary extraction solvent may be increased by 5-15 wt %, for example, by 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, or 15 wt % or higher, based on the total weight of the extract, as compared to the tea plant root extract extracted with the primary extraction solvent.

In an exemplary embodiment, the tea plant root extract may be extracted with 70% ethanol as a primary extraction solvent and then fractionated with butanol as a secondary extraction solvent. For example, the saponin content of the tea plant root extract extracted with 70% ethanol as a primary extraction solvent may be about 55.8 wt % based on the total weight of the extract, and the saponin content of the extract obtained by fractionating the tea plant root extract with butanol as a secondary extraction solvent may be about 67.6 wt %. Accordingly, the saponin content of the extract may be increased by about 11.8 wt % through the fractionation.

In an aspect, the tea plant root extract may be one that has undergone one or more of filtration, concentration, separation or drying processes after the extraction with the extraction solvent. In particular, the tea plant root extract may be one that has undergone one or more filtration process.

In an aspect, after the extraction, the extract may be concentrated under reduced pressure in a distillation apparatus equipped with a cooling condenser at an appropriate temperature, specifically at about 50° C.

However, the tea plant root extract according to the present disclosure may be obtained through extraction according to a common method in the art, without being limited to the above-described method.

In an aspect of the present disclosure, the composition may contain the tea plant root extract in an amount of 0.000001-40 wt % based on the total weight of the composition. When the content of the extract is 0.000001-40 wt %, superior effect of treating skin damage caused by fine dust, effect of reinforcing skin barrier and anti-aging and anti-inflammatory effects can be achieved with the composition containing the tea plant root extract.

Specifically, the content may be 0.0000001 wt % or higher, 0.0000005 wt % or higher, 0.0000007 wt % or higher, 0.0000009 wt % or higher, 0.000001 wt % or higher, 0.000002 wt % or higher, 0.000004 wt % or higher, 0.000006 wt % or higher, 0.000008 wt % or higher, 0.00001 wt % or higher, 0.00003 wt % or higher, 0.00005 wt % or higher, 0.00007 wt % or higher, 0.00009 wt % or higher, 0.0001 wt % or higher, 0.0003 wt % or higher, 0.0005 wt % or higher, 0.0007 wt % or higher, 0.0009 wt % or higher, 0.001 wt % or higher, 0.01 wt % or higher, 0.1 wt % or higher, 1 wt % or higher, 3 wt % or higher, 5 wt % or higher, 7 wt % or higher, 9 wt % or higher, 10 wt % or higher, 13 wt % or higher, 15 wt % or higher, 17 wt % or higher, 19 wt % or higher, 21 wt % or higher, 23 wt % or higher, 25 wt % or higher, 27 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher, or 39 wt % or higher, and may be 40 wt % or lower, 39 wt % or lower, 38 wt % or lower, 37 wt % or lower, 36 wt % or lower, 35 wt % or lower, 34 wt % or lower, 33 wt % or lower, 32 wt % or lower, 31 wt % or lower, 30 wt % or lower, 29 wt % or lower, 28 wt % or lower, 26 wt % or lower, 24 wt % or lower, 22 wt % or lower, 20 wt % or lower, 18 wt % or lower, 16 wt % or lower, 14 wt % or lower, 12 wt % or lower, 10 wt % or lower, 9 wt % or lower, 8 wt % or lower, 6 wt % or lower, 4 wt % or lower, 2 wt % or lower, 1 wt % or lower, 0.1 wt % or lower, 0.09 wt % or lower, 0.04 wt % or lower, 0.01 wt % or lower, 0.006 wt % or lower, 0.001 wt % or lower, 0.0009 wt % or lower, 0.0007 wt % or lower, 0.00005 wt % or lower, 0.00003 wt % or lower, 0.00001 wt % or lower, 0.000009 wt % or lower, 0.000007 wt % or lower, 0.000005 wt % or lower, 0.000003 wt % or lower, 0.000001 wt % or lower, 0.0000009 wt % or lower, 0.0000007 wt % or lower, 0.0000005 wt % or lower, 0.0000003 wt % or lower, 0.0000002 wt % or lower, 0.0000001 wt % or lower, or 0.00000009 wt % or lower, although not being limited thereto.

Another aspect of the present disclosure includes a use of the composition for treating skin damage caused by fine dust.

As used herein, "fine dust" refers to very small particulate matter invisible to human eyes, which floats or flutters in the atmosphere for a long time. It may refer to dust with a particle diameter of 10 μm or smaller. In particular, the particulate matter having a particle diameter of 2.5 μm or smaller is called "ultrafine dust". In the present disclosure, the term "fine dust" is intended to include "ultrafine dust".

As used herein, the term "treatment" refers to effective protection of skin cells from irritation and inhibition, prevention or restoration (recovery) of change in the expression level of a specific gene by the irritation.

In another aspect, the present disclosure provides a method for treating skin damage of a subject caused by fine dust, wherein the method includes a step of administering an effective amount of a tea plant root extract to a subject in need thereof.

In another aspect, the present disclosure provides a use of a tea plant root extract for preparing a composition for treating skin damage caused by fine dust.

In another aspect, the present disclosure provides a tea plant root extract for treating skin damage caused by fine dust.

In another aspect, the present disclosure provides a composition for inhibiting skin cell damage caused by fine dust by regulating the expression level of a specific gene in skin cells damaged by fine dust to a normal level.

Specifically, the gene in skin cells the expression level of which is affected by fine dust includes IL-36G (NM_019618), S100A7 (NM_002963), S100A8 (NM_002964), XDH (NM_000379), etc. Since the IL-36G (NM_019618), S100A7 (NM_002963), S100A8 (NM_002964) and XDH (NM_000379) are genes the expression level of which is increased by fine dust, skin cell damage may be inhibited by inhibiting the expression level of these genes and regulating it to a normal level.

The genes used in the present disclosure, the expression level of which is increased by fine dust, are listed in Table 1. Table 1 shows the genes the expression level of which is increased by fine dust. In the table, the "name" is the GeneBank accession ID of the NCBI, the "gene symbol" is the official gene symbol, and the "gene title" is the name of each gene. They are described in the non-patent document 1.

TABLE 1

| \multicolumn{3}{c}{Increased genes} | | |
|---|---|---|
| Name | Gene symbol | Gene title |
| NM_002963 | S100A7 | S100 calcium binding protein A7 |
| NM_032563 | LCE3D | Late cornified envelope 3D |
| NM_019618 | IL36G | Interleukin 36, gamma |
| NM_000576 | IL1B | Interleukin 1, beta |
| NM_000575 | IL1A | Interleukin 1, alpha |
| NM_000963 | PTGS2 | Cyclooxygenase-2 (COX-2) |
| NM_000379 | XDH | Xanthine dehydrogenase |

Another aspect of the present disclosure may include a use of the composition of the present disclosure for reinforcing skin barrier. Specifically, the composition may be a composition for reinforcing skin barrier, which contains a tea plant root extract as an active ingredient.

In another aspect, the present disclosure provides a method for reinforcing skin barrier of a subject, wherein the method includes a step of administering an effective amount of a tea plant root extract to a subject in need thereof.

In another aspect, the present disclosure provides a use of a tea plant root extract for preparing a composition for reinforcing skin barrier.

In another aspect, the present disclosure provides a tea plant root extract for reinforcing skin barrier.

In another aspect, the present disclosure provides a composition for reinforcing skin barrier by regulating the expression level of a specific gene in skin cells damaged by an irritation weakening skin barrier to a normal level.

Specifically, in an aspect of the present disclosure, the genes in skin cells the expression level of which is affected by an irritation weakening skin barrier include IL-36G (NM_019618), S100A7 (NM_002963), S100A8 (NM_002964), etc. Since the IL-36G (NM_019618), S100A7 (NM_002963) and S100A8 (NM_002964) are genes the expression level of which is increased by an irritation weakening skin barrier, the skin barrier may be reinforced by inhibiting the expression level of these genes and regulating it to a normal level.

The genes used in the present disclosure, the expression level of which is increased by an irritation weakening skin barrier, are listed in Table 2. In the table, the "name" is the GeneBank accession ID of the NCBI, the "gene symbol" is the official gene symbol, and the "gene title" is the name of each gene.

TABLE 2

| \multicolumn{3}{c}{Increased genes} | | |
|---|---|---|
| Name | Gene symbol | Gene title |
| NM_019618 | IL36G | Interleukin 36, gamma |
| NM_002963 | S100A7 | S100 calcium binding protein A7 |
| NM_002964 | S100A8 | S100 calcium binding protein A8 |

Another aspect of the present disclosure may include an anti-aging use or an anti-inflammatory use of the composition of the present disclosure. Specifically, the composition may be an anti-aging composition containing a tea plant root extract as an active ingredient, or an anti-inflammatory composition containing a tea plant root extract as an active ingredient.

In another aspect, the present disclosure provides a method for anti-aging or anti-inflammation of a subject, which includes a step of administering an effective amount of a tea plant root extract to a subject in need thereof.

In another aspect, the present disclosure provides a use of a tea plant root extract for preparing an anti-aging or anti-inflammatory composition.

In another aspect, the present disclosure provides a tea plant root extract for anti-aging or anti-inflammation.

In another aspect, the present disclosure provides a composition which inhibits inflammation or aging by regulating the expression level of a specific gene in skin cells damaged by an inflammatory or aging irritation to a normal level.

In an aspect, the composition may be applied to keratinocytes.

Specifically, in an aspect of the present disclosure, the genes in skin cells the expression level of which is affected by an inflammatory or aging irritation may include XDH (NM_000379). Since the XDH (NM_000379) is a gene the expression level of which is increased by an inflammatory or aging irritation, inflammation or aging may be inhibited by inhibiting the expression level of the gene and regulating it to a normal level.

The gene used in the present disclosure, the expression level of which is increased by an inflammatory or aging irritation, is describe in Table 3. In the table, the "name" is the GeneBank accession ID of the NCBI, the "gene symbol" is the official gene symbol, and the "gene title" is the name of each gene.

TABLE 3

| \multicolumn{3}{c}{Increased gene} | | |
|---|---|---|
| Name | Gene symbol | Gene title |
| NM_000379 | XDH | Xanthine dehydrogenase |

The expression level of the genes or proteins described above may be analyzed using various analysis methods known in the art, such as microarray, PCR, NGS (next-generation sequencing), western blot, northern blot, ELISA, radioimmunoassay, radioimmunodiffusion, immunohistochemical staining, immunoprecipitation assay, etc.

Fine dust causes skin cell damage, which induces inflammation and further aggravates the skin cell damage. This vicious cycle of skin cell damage can be treated with a tea plant root extract and, as a result, the skin condition can be improved.

In an aspect of the present disclosure, the composition may be a cosmetic composition, a pharmaceutical composition or a functional health food composition.

The cosmetic composition may be, for example, various cosmetics such as a cream, a lotion, etc., as well as a cleaner, a face wash, a soap, a beauty care solution, etc.

In an aspect, the cosmetic composition containing a tea plant root extract of the present disclosure may be in the form of a solution, an emulsion, a viscous mixture, etc.

That is to say, in an aspect, the formulation of the cosmetic composition of the present disclosure is not particularly limited. For example, the formulation may be an emulsion, a cream, a toner, an essence, a pack, a gel, a powder, a makeup base, a foundation, a lotion, an ointment, a patch, a cosmetic solution, a cleansing foam, a cleansing cream, a cleansing water, a body lotion, a body cream, a body oil, a body essence, a shampoo, a rinse, a body cleanser, a soap, a hair dye, a spray, etc.

Ingredients other than the tea plant root extract may be selected and added to the cosmetic composition of each formulation without difficulty by those skilled in the art in consideration of the formulation or purpose of use.

In addition, in an aspect, the cosmetic composition of the present disclosure may contain one selected from a group consisting of a water-soluble vitamin, an oil-soluble vitamin, a polypeptide, a polysaccharide, a sphingolipid and a seaweed extract.

In addition, in an aspect, the cosmetic composition of the present disclosure may contain ingredients that are generally used in cosmetics in addition to the essential ingredient, if necessary.

Examples of the additional ingredients include oils and fats, moisturizers, emollients, surfactants, organic and inorganic pigments, organic powders, UV absorbers, preservatives, sterilizers, antioxidants, plant extracts, pH adjusters, alcohols, colorants, fragrance, blood circulation stimulants, skin coolers, antiperspirants, purified water, etc.

However, the ingredients that may be contained in the cosmetic composition are not limited thereto. Also, the amount of any of the ingredients may be determined within a range not negatively affecting the purpose and effect of the present disclosure.

In an aspect, the pharmaceutical composition containing a tea plant root extract of the present disclosure may further contain a suitable carrier, excipient and diluent commonly used for preparation of pharmaceutical compositions.

The pharmaceutical composition containing the tea plant root extract may be formulated into any form suitable for pharmaceutical preparations, including oral formulations such as a tablet, a capsule, a powder, a syrup, etc. and formulations for external application to skin such as an ointment, a gel, a cream, a patch, a spray, etc. according to common methods.

In general, it is to be understood that the actual dosage of the active ingredient administered by the pharmaceutical composition should be determined in light of various relevant factors such as the severity of the symptom, the selected administration route, the age, gender, body weight and health condition of a subject, etc. In general, the dosage of the active ingredient may be 0.0001-3000 mg/kg/day, for example, 10-500 mg/kg/day.

In the functional health food composition according to an aspect of the present disclosure, the health food may refer to a food prepared from nutrients which are likely to be deficient in normal diets or raw materials or ingredients (functional raw materials) with functions useful for the human body, and which maintain and improve health by maintaining the normal function of the human body or activating physiological functions, although not being limited thereto. The health food may be prepared and processed into the form of a tablet, a capsule, a powder, a granule, a liquid, a pill, etc. However, the formulation is not limited thereto, and it may be prepared and processed into any form under the law.

Specifically, a health beverage composition is not particularly limited in ingredients other than the above-described substance contained in the predetermined ratio as an essential ingredient. It may contain various flavoring agents or natural carbohydrates as additional ingredients as in common beverages. Examples of the natural carbohydrates are conventional sugars such as a monosaccharide, a polysaccharide, a cyclodextrin, etc. and sugar alcohols such as xylitol, sorbitol, erythritol, etc. Also, natural flavoring agents (thaumatin, stevia extract (e.g., rebaudioside A, glycyrrhizin, etc.)) and synthetic flavoring agents (e.g., saccharin, aspartame, etc.) may be used as the flavoring agent.

In general, it is to be understood that the actual dosage of the active ingredient administered by the functional health food composition should be determined in light of various relevant factors such as the severity of the symptom, the selected administration route, the age, gender, body weight and health condition of a subject, etc. In general, the dosage of the active ingredient may be 0.0001-1000 mg/kg/day, for example, 0.02-6 mg/kg/day.

Hereinafter, the constitution and effect of the present disclosure will be described in more detail with reference to examples. However, the following examples are provided for illustrative purposes only to facilitate understanding of the present disclosure, and the scope of the present disclosure is not limited thereto.

[Example 1] Preparation of Tea Plant Root Ethanol Extract

The root of tea plant (*Camellia sinensis* L.) acquired from Jeju Osulloc Farm was washed with purified water, dried and then prepared into fine powder. 100 g of the obtained tea plant root powder was added to 1 L of a 70% aqueous ethanol solution, extracted by stirring at room temperature for at least 12 hours, and then filtered through Whatman No. 2 filter paper. The obtained extract was concentrated under reduced pressure at 50° C. using a distillation apparatus equipped with a cooling condenser and then dried to obtain a tea plant root 70% ethanol extract (dry weight=21.05 g). The obtained tea plant root 70% ethanol extract had a saponin content of about 55.8 wt % based on the total weight of the extract.

[Example 2] Preparation of Butanol Fraction of Tea Plant Root Ethanol Extract

After adding 10 g of the extract obtained in Example 1 dissolved in 200 mL of distilled water into a 1-L separatory funnel, 200 mL of butanol was added and then mixed well by shaking. After complete separation into two layers, the upper layer (butanol layer) was taken. The lower layer (aqueous layer) was extracted two more times by repeating the above procedure using a separatory funnel. After combining all the upper layers obtained in the respective extraction procedures, followed by concentration under reduced pressure at 50° C. using a distillation apparatus equipped with a cooling condenser and drying, a butanol fraction (dry weight=4.83 g) of the tea plant root ethanol extract was obtained. The obtained butanol fraction of the tea plant root ethanol extract had a saponin content of about 67.6 wt % based on the total weight of the extract.

[Example 3] Collection and Extraction of Fine Dust

Fine dust was collected using a low-volume air sampler (Sensidyne, Gillian, Fla., USA). The filter and denuder of a filter pack were replaced around 10:00 am on each measurement day, and the sample was collected for about 24 hours. Fine dust was collected daily for 28 days in an area downwind from Seoul, Korea (on the rooftop of a six-story building (Hankuk University of Foreign Studies, Center for International Studies, Residence Hall), Cheoin-gu, Yongin-si, Gyeonggi-do). Sampling time was recorded by checking the time while a vacuum pump was operated using a timer. Sampling rate, which was set to 16.7 L/min, was measured when the sampling was started and finished using a flow meter (Model 4143, TSI Inc.). A Teflon filter loaded into the filter pack was weighed before and after the sampling. Before weighing the Teflon filter, it was settled for 24 hours in a desiccator (Nikko, Japan) of 40% relative humidity. The weight was measured twice using an electronic balance (DVG215CD, Ohaus) to the five digits to the right of the decimal point and then averaged. Also, after the sampling, the filter was weighed twice after settlement in a desiccator for 24 hours. Mass concentration was calculated by comparing with the weight measured before the sampling. The fine dust was extracted as follows. The Teflon filter was soaked in 1 mL of ethanol. After adding 14 mL of DW so that the water level reached the aerosol sampling surface of the filter, followed by capping, extraction was conducted for 30 minutes by sonication. After completely removing water from the filter in a desiccator for 48 hours to minimize error, the weight of the filter before and after the extraction was measured using a high-precision balance (Mettler Toledo Company) which can measure up to 0.1 mg.

[Example 4] Culturing of (Human Normal) Keratinocytes

Keratinocytes (human normal epidermal keratinocytes) purchased from Lonza, Inc. (Walkersville, Md., USA) were subcultured and then cultured in a $CO_2$ incubator under the condition of 37° C. and 5% $CO_2$. The cells were cultured according to Lonza's guidelines. The KGM-2 bullet kit CC-3107 in which the KGM-2 bullet kit CC-4152 (BPE (bovine pituitary extract), human epidermal growth factor (hEGF), insulin, hydrocortisone, transferrin, epinephrine and gentamycin sulfate+amphotericin-B (GA-1000)) was added to 500 mL of a KBM-2 (KBM™-2, CC-3103) medium was used.

[Example 5] Treatment of (Human Normal) Keratinocytes with Fine Dust and Measurement of Cytotoxicity In order to investigate the effect of treatment with fine dust on cytotoxicity, MTT assay was performed with the (normal human) keratinocytes according to the method of Mossman et al. (*J. Immunol. Methods*, 65, 55-63, 1983).

Specifically, a 24-well plate was used. The fine dust obtained in Example 2, with a diameter of 2.5 µm, was dispersed in purified water to prepare a fine dust dispersion. Then, the fine dust dispersion was applied to the cells cultured under the conditions of Example 3, with $2.5 \times 10^5$ cells per well, followed by culturing for 24 hours. Then, the cells were mixed with 5 mg/mL of MTT (3-4,5-dimethyl-thiazol-2,5-diphenyltetrazolium bromide) and further cultured at 37° C. for 3 hours. The medium was then removed and the formazan crystal formed was dissolved in 500 µL of DMSO. The lysate was aliquoted to a 96-well plate and the OD value was measured at 540 nm. The measurement result is shown in FIG. 1.

As shown in FIG. 1, the concentration achieving 80% cell viability ($IC_{20}$) for cytotoxicity caused by the dispersion obtained by dispersing the fine dust with a diameter of 2.5 µm or smaller was 12.5 µg/mL.

[Example 6] Investigation of Change in Genes in Cells Due to Fine Dust by Next-Generation Sequencing For RNA-base sequence data processing and analysis, reference was made to the general analysis technique developed by Trapnell et al. (2012). The RNA-seq data quality was determined using FastQC (http://www.bioinformatics.babraham.ac.uk/projects/fastqc/). The base and adapter sequences with low accuracy were removed using FASTX (http://hannonlab.cshl.edu/fastx_toolkit/). Then, alignment was performed using Tophat (Trapnell et al., 2009) and a human genome (hg19), and the amount of data of each sample was determined using EVER-seq renamed to RSeQC (Wang et al., 2012). In addition, the expression level of transcripts was quantified using Cufflinks, and transcription levels were compared between the sample treated with the fine dust dispersion and a normal sample (Trapnell et al., 2010). A stringent cut-off of 2.0-fold change, with the FDR-adjusted p-value <0.05, was used to determine the gene that showed significant difference in expression upon treatment with the dispersion of fine dust with a diameter of 2.5 µm. The measurement result is shown in FIGS. 2A-2D.

[Example 7] Real-Time RT-PCR

The normal human keratinocytes cultured in Example 4 were treated with the fine dust having a diameter of 2.5 µm extracted in Example 3, with 12.5 µg per 1 mL of the cell culture medium. Then, the relative mRNA expression level was measured using the primers (Applied Biosystems TaqMan® primers) of the genes described in Table 4. The tea plant root extract and the butanol fraction prepared in Examples 1 and 2 were used.

TABLE 4

| | Increased genes | |
|---|---|---|
| Name | Gene symbol | TaqMan ® primers |
| NM_019618 | IL36G | Hs00219742_m1 |
| NM_002963 | S100A7 | Hs00161488_m1 |
| NM_002964 | S100A8 | Hs00374263_m1 |
| NM_000379 | XDH | Hs00166010_m1 |

The medium was treated with the tea plant root extract and the tea plant root saponin extract at 1 ppm and 5 ppm, respectively. After 24 hours, the culture solution was removed and the cells were washed with 2 mL of phosphate-buffered saline (PBS). Then, RNA was isolated from the cells using a Trizol reagent (Invitrogen, Carlsbad, Calif., USA). The isolated RNA was further purified with the QIAGEN RNeasy kit (QIAGEN, Valencia, Calif.). Then, the quality of the RNA was determined using the Agilent 2100 BioAnalyzer (Agilent Technologies, Santa Clara, Calif., USA). cDNA was synthesized from the RNA using the Superscript reverse transcriptase (RT) kit (Invitrogen, Carlsbad, Calif.). The cDNA was quantitatively analyzed by real time-reverse transcription polymerase chain reaction (Q-RT-PCR) using the primers shown in Table 4. The change in the expression pattern of genes was evaluated by real-time PCR using the TaqMan gene expression assay kit (Applied Biosystems, Foster City, Calif.). The result is shown in FIGS. 2A-2D. Both of the Q-RT-PCR and the real-time PCR were performed according to the standard protocols distributed by Life Technologies. Specifically, 40 cycles of 95° C. for 20 seconds, 95° C. for 3 seconds and 60° C. for 30 seconds were performed.

FIGS. 2A-2D show that there exist genes the expression level of which is increased or decreased in the skin cells irritated by fine dust. Also, it was found that the expression level of the interleukin 36 gamma (IL-36G), S100 calcium-binding protein A7 (S100A7), S100 calcium-binding protein A8 (S100A8) and xanthine dehydrogenase (XDH) genes is decreased by treatment with the tea plant root extract.

Therefore, it was found that the tea plant root extract effectively protects skin cells from irritation by fine dust and inhibits or prevents the change in the expression level of the above-described specific genes due to the irritation, thereby returning the expression level to a normal level. In addition, it was found that the tea plant root extract effectively protects skin cells from skin cell damage caused by skin barrier-weakening irritation and inhibits or prevents the change in the expression level of the above-described specific genes due to the irritation, thereby returning the expression level to a normal level. In addition, it was found that the tea plant root extract effectively protects skin cells from skin cell damage caused by inflammatory or aging irritation and inhibits or prevents the change in the expression level of the above-described specific genes due to the irritation, thereby returning the expression level to a normal level.

Hereinafter, formulation examples of the compositions according to the present disclosure will be described. However, the cosmetic composition, pharmaceutical composition and health functional food composition may be formulated into various other forms. These examples are for illustrative purposes only and are not intended to limit the scope of the present disclosure.

[Formulation Example 1] Tablet 100 mg of the tea plant root extract according to the present disclosure, 400 mg of lactose, 400 mg of corn starch and 2 mg of magnesium stearate were mixed and subjected to a tableting process according to a conventional method for preparing tablets to prepare a tablet.

TABLE 5

| Ingredients | Contents (mg) |
|---|---|
| Tea plant root extract | 100 |
| Lactose | 400 |
| Corn starch | 400 |
| Magnesium stearate | 2 |

[Formulation Example 2] Capsule 100 mg of the tea plant root extract according the present disclosure, 400 mg of lactose, 400 mg of corn starch and 2 mg of magnesium stearate were mixed and filled in a gelatin capsule according to a conventional method for preparing capsules to prepare a capsule.

TABLE 6

| Ingredients | Contents (mg) |
|---|---|
| Tea plant root extract | 100 |
| Lactose | 400 |
| Corn starch | 400 |
| Magnesium stearate | 2 |

[Formulation Example 3] Granule 50 mg of the tea plant root extract according to the present disclosure, 250 mg of anhydrous crystalline glucose and 550 mg of starch were mixed and formulated into granules using a fluidized-bed granulator. The granules were then filled in a pouch.

TABLE 7

| Ingredients | Contents (mg) |
|---|---|
| Tea plant root extract | 50 |
| Anhydrous crystalline glucose | 250 |
| Starch | 550 |

[Formulation Example 4] Soap

TABLE 8

| Ingredients | Contents (%) |
|---|---|
| Tea plant root extract | 5.00 |
| Oil and fat | q.s. |
| Sodium hydroxide | q.s. |
| Sodium chloride | q.s. |
| Fragrance | q.s. |
| Purified water | Balance |

[Formulation Example 5] Lotion

TABLE 9

| Ingredients | Contents (%) |
|---|---|
| Tea plant root extract | 5.00 |
| Magnesium L-ascorbic acid-2-phosphate | 1.00 |
| Water-soluble collagen (1% aqueous solution) | 1.00 |
| Sodium citrate | 0.10 |
| Citric acid | 0.05 |
| Licorice extract | 0.20 |
| 1,3-Butylene glycol | 3.00 |
| Purified water | Balance |

[Formulation Example 6] Cream

TABLE 10

| Ingredients | Contents (%) |
|---|---|
| Tea plant root extract | 3.00 |
| Polyethylene glycol monostearate | 2.00 |
| Self-emulsifying glycerin monostearate | 5.00 |
| Cetyl alcohol | 4.00 |
| Squalene | 6.00 |
| Glyceryl tri(2-ethylhexanoate) | 6.00 |
| Sphingoglycolipid | 1.00 |
| 1,3-Butylene glycol | 7.00 |
| Purified water | Balance |

[Formulation Example 7] Ointment

TABLE 11

| Ingredients | Contents (%) |
| --- | --- |
| Tea plant root extract | 5.00 |
| Polyvinyl alcohol | 13.00 |
| Magnesium L-ascorbic acid-2-phosphate | 1.00 |
| Lauroyl hydroxyproline | 1.00 |
| Water-soluble collagen (1% aqueous solution) | 2.00 |
| 1,3-Butylene glycol | 3.00 |
| Ethanol | 5.00 |
| Purified water | Balance |

[Formulation Example 8] Beauty Care Solution

TABLE 12

| Ingredients | Contents (%) |
| --- | --- |
| Tea plant root extract | 3.00 |
| Hydroxyethylene cellulose (2% aqueous solution) | 12.00 |
| Xanthan gum (2% aqueous solution) | 2.00 |
| 1,3-Butylene glycol | 6.00 |
| Concentrated glycerin | 4.00 |
| Sodium hyaluronate (1% aqueous solution) | 2.00 |
| Purified water | Balance |

[Formulation Example 9] Health Food

TABLE 13

| Ingredients | Contents |
| --- | --- |
| Tea plant root extract | 2 mg |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

[Formulation Example 10] Health Drink

TABLE 14

| Ingredients | Contents |
| --- | --- |
| Tea plant root extract | 50 mg |
| Citric acid | 1000 mg |
| Oligosaccharide | 100 g |
| Taurine | 1 g |
| Purified water | balance |

The invention claimed is:

1. A method for treating skin damage caused by fine dust comprising administering an effective amount of a tea plant (Camellia sinensis) root extract to a subject in need thereof, wherein the subject has increased expression of one or more selected from a group consisting of IL-36G (NM 019618), S100A7 (NM 002963), S100A8 (NM 002964) and XDH (NM 000379),
wherein the tea plant root extract is one that has been primarily extracted with anhydrous or hydrated ethanol and then secondarily fractionated with anhydrous or hydrated butanol.

2. The method according to claim 1, wherein the tea plant root extract is an extract comprising a saponin.

3. The method according to claim 2, wherein the tea plant root extract comprises the saponin in an amount of 30-70 wt % based on the total weight of the extract.

4. The method according to claim 1, wherein the tea plant root extract is administered in a form of a composition and the tea plant root extract is comprised in an amount of 0.000001-40 wt % based on the total weight of the composition.

5. The method according to claim 1, wherein said administrating an effective amount of the tea plant root extract inhibits the expression of one or more selected from a group consisting of IL-36G (NM_019618), S100A7 (NM_002963) and S100A8 (NM_002964).

6. The method according to claim 1, wherein said administrating an effective amount of the tea plant root extract inhibits the expression of one or more selected from a group consisting of IL-36G (NM_019618), S100A7 (NM_002963) and S100A8 (NM_002964).

7. The method according to claim 1, wherein said administrating an effective amount of the tea plant root extract inhibits the expression of XDH (NM_000379).

8. The method according to claim 1, wherein the tea plant root extract is applied to keratinocytes.

9. The method according to claim 1, wherein the fine dust has a particle size of PM 2.5 or smaller.

10. The method according to claim 1, wherein the tea plant root extract is administered at a dosage of 10-500 mg/kg/day.

11. The method according to claim 1, wherein the tea plant root extract is administered in a form of a cosmetic composition.

12. The method according to claim 1, wherein the tea plant root extract is administered in a form of a pharmaceutical composition.

13. The method according to claim 1, wherein the tea plant root extract is administered in a form of a functional health food composition.

* * * * *